United States Patent
Hayton et al.

(10) Patent No.: US 12,357,764 B1
(45) Date of Patent: Jul. 15, 2025

(54) ATTACHMENT MECHANISM, MODULE AND ASSEMBLY HEREWITH

(71) Applicant: Sanofi, Paris (FR)

(72) Inventors: Paul Hayton, Bristol (GB); Michael Jugl, Frankfurt am Main (DE); Ralph Donald Quentin Collings, Bristol (GB); Jakub Sekula, Bristol (GB); Martin Vitt, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/590,711

(22) Filed: Feb. 28, 2024

(51) Int. Cl.
  *A61M 5/315* (2006.01)
  *A61M 5/24* (2006.01)
  (Continued)

(52) U.S. Cl.
  CPC ...... *A61M 5/31568* (2013.01); *A61M 5/2422* (2013.01); *A61M 5/3157* (2013.01);
  (Continued)

(58) Field of Classification Search
  CPC .......... A61M 5/00; A61M 5/178; A61M 5/20; A61M 5/2033; A61M 5/24; A61M 5/2422; A61M 5/28; A61M 5/31; A61M 5/31525; A61M 5/31528; A61M 5/31533; A61M 5/31535; A61M 5/31541; A61M 5/31545; A61M 5/31546; A61M 5/3155; A61M 5/31551; A61M 5/31553; A61M 5/31555; A61M 5/31565; A61M 5/31566; A61M 5/31568; A61M 5/3157; A61M 5/31573; A61M 5/31576; A61M 5/3158; A61M 5/31585; A61M 5/3159; A61M 5/31593; A61M 5/31548; A61M 5/31578;
  (Continued)

(56) References Cited

U.S. PATENT DOCUMENTS

| 2,475,939 A | 7/1949 | Applezweig |
| 3,080,867 A | 3/1963 | Eichinger |
| (Continued) | | |

FOREIGN PATENT DOCUMENTS

| EP | 1570876 B1 | 12/2009 |
| EP | 2814547 B1 | 7/2015 |
| (Continued) | | |

OTHER PUBLICATIONS

Hamers-Casterman et al., "Naturally occurring antibodies devoid of light chains," Nature, Jun. 3, 1993, 363(6428):446-448.

(Continued)

*Primary Examiner* — Kevin C Sirmons
*Assistant Examiner* — Alexandra Lalonde
(74) *Attorney, Agent, or Firm* — Fish & Richardson P.C.

(57) ABSTRACT

The present disclosure is generally directed to an attachment mechanism suitable for attaching for example a module to an object that is essentially cylindrical or polygonal in cross-section, e.g. to a portion of a drug delivery device. Further, the disclosure is directed to an electronic system, which is configured to be, e.g. releasably, attached to the drug delivery device as well as an assembly comprising the the electronic system as well as the drug delivery device. The attachment mechanism may comprise a housing, a gripping portion with at least one gripping ring and an actuator for operating the gripping portion between an open condition and a clamping condition.

9 Claims, 2 Drawing Sheets

(52) U.S. Cl.
CPC ... *A61M 5/3158* (2013.01); *A61M 2205/3375* (2013.01); *A61M 2205/581* (2013.01)

(58) Field of Classification Search
CPC .... A61M 2005/2006; A61M 2005/202; A61M 2005/2026; A61M 2005/3125; A61M 2005/3126; A61M 2005/3142; A61M 2005/3154; A61M 2005/31588; A61M 2205/3375; A61M 2205/35; A61M 2205/3546; A61M 2205/3569; A61M 2205/3576; A61M 2205/3584; A61M 2205/50; A61M 2205/502; A61M 2205/505; A61M 2205/58; A61M 2205/581; A61M 2205/6027; G16H 20/17
See application file for complete search history.

(56) References Cited

U.S. PATENT DOCUMENTS

| | | |
|---|---|---|
| 5,693,027 A | 12/1997 | Hansen et al. |
| 6,663,602 B2 | 12/2003 | Moller |
| 7,241,278 B2 | 7/2007 | Moller |
| 9,937,294 B2 | 4/2018 | Quinn et al. |
| 2008/0306446 A1 | 12/2008 | Markussen |
| 2009/0054839 A1 | 2/2009 | Moller et al. |
| 2015/0025470 A1 | 1/2015 | Baran et al. |
| 2017/0000950 A1* | 1/2017 | Baran ............... A61M 5/31525 |
| 2021/0187200 A1 | 6/2021 | Urbanek et al. |
| 2023/0047344 A1 | 2/2023 | Scheurer et al. |

FOREIGN PATENT DOCUMENTS

| | | |
|---|---|---|
| EP | 2890434 B1 | 4/2020 |
| WO | WO 2004/068820 A2 | 8/2004 |
| WO | WO 2004/078239 A1 | 9/2004 |
| WO | WO 2005/018629 A1 | 3/2005 |
| WO | WO 2005/018721 A1 | 3/2005 |
| WO | WO 2006/003388 A2 | 1/2006 |
| WO | WO 2006/030220 A1 | 3/2006 |
| WO | WO 2009/132777 A1 | 11/2009 |
| WO | WO 2014/033195 A1 | 3/2014 |
| WO | WO 2016/198516 A1 | 12/2016 |
| WO | WO 2019/145415 A1 | 8/2019 |

OTHER PUBLICATIONS

Holt et al., "Domain antibodies: proteins for therapy," Trends in Biotechnology, Nov. 2003, 21(11):484-490.

Muyldermans, "Single domain camel antibodies: current status," Reviews in Molecular Biotechnology, Jun. 2001, 74(4):277-302.

Needle-based injection systems for medical use Requirements and test methods, Part 1: Needle injection systems, ISO 11608-1:2014(E), Third Edition, Switzerland, ISO, Dec. 15, 2014, pp. 1-13.

Ward et al., "Binding activities of a repertoire of single immunoglobulin variable domains secreted from *Escherichia coli*," Nature, Oct. 1989, 341(6242):544-546.

* cited by examiner

ATTACHMENT MECHANISM, MODULE AND ASSEMBLY HEREWITH

TECHNICAL FIELD

The present disclosure is generally directed to an attachment mechanism suitable for attaching for example a module to an object that is essentially cylindrical or polygonal in cross-section, e.g. to a portion of a drug delivery device. Further, the disclosure is directed to an electronic system, e.g. an electronic add-on module, which is configured to be, e.g. releasably, attached to a drug delivery device as well as an assembly comprising the electronic add-on module as well as the drug delivery device.

BACKGROUND

Electronic add-on modules may be used attached on to a drug delivery device, e.g. a pen-type injection device. Such drug delivery devices often comprise a housing with a container configured to receive a drug or a cartridge filled with a drug, a dose setting unit comprising a dose dial user interface, e.g. a dial grip, at least rotationally moveable with respect to the housing during dose setting and an injection user interface, e.g. a dose button, at least axially moveable with respect to the housing for causing dose dispensing, and a dose delivery unit comprising a plunger at least axially moveable with respect to the housing during dose dispensing.

Electronic add-on modules for releasable attachment to drug delivery devices can be used to measure relevant data with respect to dose setting and/or dose dispensing. Due to the different dimensions and working principles of injection devices, especially regarding dose dial user interfaces and injection user interfaces, such add-on modules are typically tailored to fit to one specific drug delivery device. This requires providing different modules for different devices.

Electronic add-on modules described in WO 2016/198516 A1 include a sleeve-like portion to be positioned over a dosage knob or dial grip of an injection device. A resilient padding is provided on the inner surface of the sleeve-like portion. The padding deforms to accommodate the dosage knob within the cavity of the sleeve-like portion.

Further, monitoring devices for attachment to an injection device are described in WO 2019/145415 A1. This add-on device comprises a coupling element adapted for accommodating the push button and the selector of an insulin pen. In order to adapt to the specific form of any dose selector, the coupling element comprises a gasket with an inner orifice, whose inner surface is similar to the external surface of the selector, such that it can slide along it and embrace it achieving a firm attachment thereto. By employing different designs for the gasket, the device can be used with any available model of drug pen. The gasket is a removable element which can be detached from the coupling element for example, to be interchanged with other gaskets for the adaptation of the device for its coupling to different models of drug pens.

SUMMARY

The present disclosure describes an improved attachment mechanism, an improved electronic add-on module suitable to be used with various different drug delivery devices and an improved assembly comprising a drug delivery device and such an electronic add-on module.

An attachment mechanism suitable for attaching a module to an object that is essentially cylindrical or polygonal in cross-section, like a drug delivery device or a portion thereof, may comprise a housing, a gripping portion and an actuator for operating the gripping portion between an open condition, i.e. a relaxed state or condition of the attachment mechanism permitting attachment or detachment, and a clamping condition, i.e. a resting state or condition in which the module is held and fixed on the object. In other words, the griping portion may be opened and closed by a user for changing between said two conditions.

According to an aspect of the present disclosure, the gripping portion preferably comprises a first gripping ring with a second longitudinal axis parallel to the first longitudinal axis of the housing and at least one spring. The first gripping ring may be guided and/or retained in the housing such that the first gripping ring is shiftable in a direction perpendicular the first and second longitudinal axes from the open condition in which the first and second longitudinal axes are closer together to the clamping condition in which the first and second longitudinal axes are further spaced from each other. The at least one spring is arranged and configured such that it biases the first gripping ring into the clamping condition. In other words, the attachment mechanism can assume various inner diameters by actuation of the gripping portion, more specifically the at least one gripping ring. This has the benefit of providing a mechanism e.g. for an add-on module which fits onto different drug delivery devices without requiring individual adapter parts. Rather, the attachment mechanism or a module with such a mechanism is configured to be put, e.g. pressed, onto injectors of varying diameters, for example from around 14 mm to 18 mm, providing secure attachment of the module via a friction fit regardless of the drug delivery device dimensions. The gripping portion may be configured to have a holding torque of at least 750 Nmm, e.g. between 1.250 Nmm and 2.500 Nmm or between 1.000 Nmm and 1.500 Nmm, for example about or exactly 1.350 Nmm, when attached to a drug delivery device component having a diameter of about 14 mm to 18 mm and when being in its clamping condition. Suitable holding torques can be achieved by selecting the at least one spring with a suitable spring force and/or by selecting the inner surface of the housing and/or the at least one gripping ring accordingly, e.g. by increasing the surface roughness and/or by providing an inner rubber or elastomeric layer.

In a simple but effective example of the present disclosure, the attachment mechanism comprises only one gripping ring and one spring biasing the gripping ring into the clamping condition of the mechanism. However, in an alternative embodiment of the present disclosure, the attachment mechanism comprises two or more gripping rings and two or more associated springs each biasing the respective gripping rings into the clamping condition of the mechanism. Providing e.g. two gripping rings and two springs may result in a more reliable attachment mechanism.

The first gripping ring may have a smaller inner diameter than the housing. An optional second gripping ring may have a smaller inner diameter than the housing, too. For example, both griping rings may be substantially arranged within the housing and the outer diameter of the gripping ring(s) may be smaller then the inner diameter of the housing by at least 1 mm, for example by 1.5 mm to 5 mm, e.g. by about 3 mm or about 4 mm, permitting shifting of the gripping ring(s) within the housing in a direction perpendicular to the respective longitudinal axes.

In the example of only one gripping ring, the at least one spring may be a compression spring interposed between a radially outer surface of the housing and a radially inner surface of the first gripping ring. In the examples of two or more gripping rings, the respective springs may be interposed between portions of the gripping rings. In more detail, the at least one spring of the first gripping ring may be a compression spring interposed between a radially outer surface of the second gripping ring and a radially inner surface of the first gripping ring and wherein the at least one further spring of the second gripping ring may be a compression spring interposed between a radially outer surface of the first gripping ring and a radially inner surface of the second gripping ring. The spring(s) may be separate spring(s) or may be an integral part of the respective gripping ring(s), e.g. a spring arm.

According to an aspect of the attachment mechanism a second gripping ring with a third longitudinal axis parallel to the first longitudinal axis of the housing and at least one further spring are provided, wherein the second gripping ring is retained in the housing such that the second gripping ring is shiftable in a direction perpendicular the first and third longitudinal axes from an open position in which the first and third longitudinal axes are closer together to a clamping condition in which the first and third longitudinal axes are further spaced from each other, and wherein the at least one further spring biases the second gripping ring into the clamping condition.

In order to permit relative radial movement of the griping rings while being retained and encased in the housing, the first gripping ring and the second gripping ring may be at least partially offset in the direction of the first longitudinal axis. The gripping rings may abut each other with axially directed surfaces, i.e. a distal surface and a proximal surface. According to a further independent aspect of the present disclosure, the gripping rings may partially overlap with each other in the axial direction.

The actuator may comprise a button portion of the first gripping ring configured to be operated to shift the first gripping ring into the open condition against the bias of the at least one spring. For example, both gripping rings have a respective button portion. The button portions may be arranged facing in opposite directions. The button portion(s) may at least partially protrude radially from the housing.

The present disclosure is based on the idea that the attachment mechanism comprises a gripper mechanism used to attach an electronic add-on module or the like smart cap device to a portion, e.g. to the dose dial grip, of an, e.g. disposable, injector pen. According to an independent aspect of the disclosure, the attachment mechanism may comprise a housing and two spring loaded rings with buttons which protrude out of the housing. The buttons may be constrained such that they can slide on one axis relative to each other and overlap. The overlapping creates an apparent reduction in the inner diameter of the ring assembly, which allows gripping a substantially cylindrical or polygonal portion of a drug delivery device of varying diameter and geometry.

In the neutral state of the attachment mechanism, i.e. in the clamping condition, the springs are extended and push the two rings towards each other, resulting in maximum radial overlap and minimum inner diameter. By pressing the two protruding buttons connected to each of the rings, the user can reduce the radial overlap amount and increase the effective inner diameter of the attachment mechanism. This allows a smooth variation of the gripper size and attachment to an arbitrary injector dial grip.

A further aspect of the present disclosure is the ability to smoothly adjust the inner diameter of the gripper portion of the attachment mechanism while providing enough compression to securely grip different dial grips or the like. This makes it possible to create a module or smart cap that is cross-platform compatible with injector pens of different brands and sizes. By utilizing a variable diameter attachment mechanism as proposed with the present disclosure, one module or smart cap could be used by a user with a prescription for several different pens.

The attachment mechanism may be used in or with an electronic add-on module which may be, e.g. releasably, attached to the drug delivery device by frictional, elastic and/or form fit engagement with the releasable gripping portion. A module according to the present disclosure comprises an attachment mechanism as defined above. An assembly according to the present disclosure comprises a drug delivery device and an electronic add-on module configured for releasable attachment to the drug delivery device.

Drug delivery devices may comprise at least a housing with a container configured to receive a drug or a cartridge filled with a drug. Further, the drug delivery device may comprise a dose setting unit and a dose delivery unit. Suitable drug delivery devices to be used with a mechanism or module according to the present disclosure are described e.g. in WO 2004/078239 A1, EP 1 570 876 B1, EP 2 814 547 B1, EP 2 890 434 B1, WO 2005/018721 A1, WO 2009/132777 A1, WO 2014/033195 A1, U.S. Pat. Nos. 5,693,027 A, 6,663,602 B2, 7,241,278 B2 or U.S. Pat. No. 9,937,294 B2. In addition to manually driven devices, the module may be used with spring driven devices as described in US 2008/0306446 A1 or US 2009/0054839_A1. However, the present disclosure is not limited to these examples of drug delivery devices. Rather, other drug delivery devices with a stationary and/or operable portion having an e.g. substantially cylindrical shape may be used with the module. For example, the drug delivery devices may comprise a user interface for selecting and/or dispensing a fixed or variable dose of a drug.

The dose setting unit may comprise a dose dial user interface, e.g. a dose dial grip, which is, at least rotationally, e.g. helically, moveable with respect to the housing during dose setting and an injection user interface at least axially moveable with respect to the housing for causing dose dispensing. The injection user interface may be a separate component part, e.g. a dose button, which may be displaced relative to the dose dial user interface for causing dose dispensing. As an alternative, the dose dial user interface and the injection user interface may be portions of one single component part, e.g. a combined dose dial and injection knob.

The electronic add-on module may comprise a first portion which comprises the attachment mechanism. The module may further comprise an optional second portion coupled to the first portion allowing relative axial movement parallel to the first longitudinal axis with respect to the first portion. The first portion may define an auxiliary dose dial user interface and may be configured to be releasably attached to the dose dial user interface of the drug delivery device such that the first portion follows the movement of the dose dial user interface and vice versa when attached to the drug delivery device. The second portion may define an auxiliary injection user interface configured to apply pressure onto the injection user interface of the drug delivery device when attached to the drug delivery device.

In an electronic add-on module configured to be releasable attached to a drug delivery device the electronic add-on module may comprise an attachment mechanism as mentioned above configured for releasable attachment to a portion of the drug delivery device, especially but not limited to a dose dial user interface, e.g. a dose dial grip. The electronic add-on module may comprise a first portion with a main housing defining a longitudinal axis coinciding with the longitudinal axis of the gripper ring(s) of the attachment mechanism, wherein the housing of the attachment mechanism may be the main housing or may be attached thereto. The electronic add-on module may further comprise a second portion coupled to the first portion allowing relative axial movement parallel to the longitudinal axis with respect to the first portion. The second portion may be a button partially received in the main housing of the first portion. In an example, the first portion may define an auxiliary dose dial user interface configured to be attached to a dose dial user interface of the drug delivery device, such that the first portion follows the movement of the dose dial user interface and vice versa when attached to the drug delivery device, and the second portion may define an auxiliary injection user interface configured to apply pressure onto an injection user interface of the drug delivery device.

The second portion may be at least partially encased by and retained in the first portion. For example, the first portion has a cavity receiving at least partially the second portion. The second portion may be axially movable relative to the first portion in a restricted manner preventing full disassembly of the first and second portions. In other words, they can be moved a limited distance relative to each other for operating the drug delivery device. A spring may be provided biasing the second portion in the proximal direction with respect to the first portion. In other words, the optional spring may hold the second portion which may be a shuttling button assembly in place while at rest and return it to its neutral position after actuation.

According to an independent aspect of the present disclosure, the second portion may comprise an electrical power source, e.g. a battery or a rechargeable cell, a printed circuit board assembly (PCBA), e.g. comprising and/or forming a control unit, a sensor arrangement, for example an acoustic sensor arrangement comprising e.g. at least one micro-phone, configured to detect a relative rotational movement between at least two component parts of the drug delivery device, a communication unit for communicating with another device, e.g. for wireless transfer of data, and/or a switch arrangement, e.g. for turning the electronic module on and off and/or for waking the module or its components from a sleeping mode or a low power consumption mode.

An assembly according to the present disclosure comprises a drug delivery device and an electronic add-on module configured for releasable attachment to the drug delivery device.

Preferably, the drug delivery device comprises: a device housing with a container configured to receive a drug or a cartridge filled with a drug, a dose setting unit comprising a dose dial user interface at least rotationally moveable with respect to the device housing during dose setting and an injection user interface at least axially moveable with respect to the device housing for causing dose dispensing, and a dose delivery unit comprising a plunger at least axially moveable with respect to the device housing during dose dispensing.

Although not required in the context of the present disclosure, the drug delivery device may optionally comprise further components such as a drive sleeve, a number sleeve, a clutch, a cap, a needle, a spring, a lead screw or the like, interacting with the dose button, the dose dial grip, the drive sleeve, the plunger and/or the housing, for example as disclosed in WO 2004/078239 A1. However, the present disclosure is not limited to the drug delivery device of WO 2004/078239 A1. Other suitable drug delivery devices to be used with such a module may comprise a dial grip for selecting a variable dose and a separate dose button for initiating or performing dose dispensing, e.g. as described in EP 1 570 876 B1,EP 2 814 547 B1, EP 2 890 434 B1, WO 2009/132777 A1, U.S. Pat. No. 6,663,602 B2,U.S. Pat. No. 7,241,278 B2 or U.S. Pat. No. 9,937,294 B2. In addition, other suitable drug delivery devices to be used with such a module may comprise a single knob forming a dial grip for selecting a variable dose and a dose button for initiating or performing dose dispensing, e.g. as described in WO 2005/018721 A1 or WO 2014/033195 A1. Still further, the drug delivery device may be a spring driven device as described in US 2008/0306446 A1 or US 2009/0054839 A1.

If the drug delivery device has a similar working principle as in the example of WO 2004/078239 A1, during dose setting components of the drug delivery device may perform the following movements. A housing may be stationary and may be used as a reference system for the further movements of other components. A plunger may be stationary and may be guided in a housing thread. A drive sleeve may be provided rotationally coupled to the dose dial grip during dose setting and rotationally constrained to the housing during dose dispensing. In other words, the drive sleeve may be guided in the housing to perform a purely axial movement during dose dispensing. The drive sleeve may perform a helical movement, i.e. a combined axial and rotational movement, and may be in threaded engagement with the plunger. A dial grip may perform a helical movement. A dose button may be free to rotate but axially constrained to the drive sleeve. For example, the dose button may be axially retained to the drive sleeve by a clutch. An optional clutch may per-form a helical movement and may couple a number sleeve to the drive sleeve. An optional clutch spring may perform an axial movement and may be guided in housing splines and may click over clutch teeth. An optional number sleeve may be permanently fixed on the dial grip and may perform a helical movement and may be guided in a housing thread. An optional last dose nut may perform a helical movement on a drive sleeve track of the drive sleeve and may be rotationally constrained to the housing. Hence, the last dose nut may perform axial movement relative to the housing and a helical movement with respect to the drive sleeve.

During dose dispensing components of the drug delivery device may perform the following movements. The housing may remain stationary as a reference system for the further movements of other components. The plunger may perform a helical movement and may be guided in the housing thread. The drive sleeve may perform a pure axial movement and may be in threaded engagement with the plunger. The dose dial grip may perform a helical movement and may be permanently fixed on the number sleeve. The dose button may perform an axial movement if coupled to the drive sleeve and/or the clutch. The optional clutch may perform pure axial movement and may de-couple the number sleeve from the drive sleeve. The optional clutch spring may perform pure axial movement and may be rotationally constrained to the clutch due to a pressure applied to the dose button. The optional number sleeve may perform a helical movement and may be guided in the housing thread.

The optional last dose nut may maintain its axial position on the drive sleeve track and may be rotationally constrained to the housing.

In an assembly according to the present disclosure, when the module is attached to the dose dial user interface of the drug delivery device, the gripping portion, especially the gripper ring(s), may be elastically biased to abut the dose dial user interface in a form fit and/or friction fit when in its clamping condition.

According to an independent aspect of the present disclosure, the assembly comprises a drug delivery device having a clicker mechanism generating an acoustic feedback signal during specific use conditions, e.g. at least during dose setting. Such a feedback signal may be detected by the electronic module and the module may determine an amount of dose selected and/or dispensed. For example, the clicker mechanism may generate one clicking sound for every IU dispensed, like e.g. in WO 2004/078239 A1, WO 2014/033195 A1, WO 2005/018721 A1 or EP 1 570 876 B1.

The electronic add-on module may be an electronic dose recording system for determining, storing and/or transmitting data indicative of at least a condition of the drug delivery device or its use. For example, the system may detect if the drug delivery device is switched between a dose setting mode and a dose dispensing mode and vice versa. In addition or as an alternative, the system may detect if a dose is set and/or if a dose is dispensed. Still further, the system may detect the amount of dose selected and/or the amount of dose dispensed. Preferably, the electronic add-on module is configured such that it may be switched from a first state having lower energy consumption into a second state having higher energy consumption. This may be achieved by operation of the electronic add-on module, especially by actuating the microswitch. As an alternative, the module may be provided with a wake up functionality which does not require a separate actuation action. The first state may be a sleeping mode and the second mode may be a detection and/or communication mode. As an alternative, an electronic control unit may issue a command, e.g. a signal, to another unit of the electronic dose recording system such that this unit is switched on or rendered operational.

The electronic add-on module may further comprise a communication unit for communicating with another device, e.g. a wireless communications interface for communicating with another device via a wireless network such as Wi-Fi or Bluetooth, or even an interface for a wired communications link, such as a socket for receiving a Universal Serial Bus (USB), mini-USB or micro-USB connector. Preferably, the electronic add-on module comprises an RF, Wi-Fi and/or Bluetooth unit as the communication unit. The communication unit may be provided as a communication interface between the electronic add-on module and the exterior, such as other electronic devices, e.g. mobile phones, personal computers, laptops and so on. For example, dose data may be transmitted by the communication unit to the external device. The dose data may be used for a dose log or dose history established in the external device.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des (B30) human insulin, B29-N-omegacarboxypentadecanoyl-gamma-L-glutamyl-des (B30) human insulin (insulin degludec, Tresiba®); B29-N-(N-lithocholyl-gamma-glutamyl)-des (B30) human insulin; B29-N-(w-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Languagelenatide/HM-11260C (Efpeglenatide), HM-15211, CM-3, GLP1 Eligen, ORMD-0901, NN-9423, NN-9709, NN-9924, NN-9926, NN-9927, Nodexen, ViadorGLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the devices of the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, small modular immunopharmaceuticals (SMIP), binding-domain immunoglobulin fusion proteins, camelized antibodies, and immunoglobulin single variable domains. Additional examples of antigen-binding antibody fragments are known in the art.

The term "immunoglobulin single variable domain" (ISV), interchangeably used with "single variable domain", defines immunoglobulin molecules wherein the antigen binding site is present on, and formed by, a single immunoglobulin domain. As such, immunoglobulin single variable domains are capable of specifically binding to an epitope of the antigen without pairing with an additional immunoglobulin variable domain. The binding site of an immunoglobulin single variable domain is formed by a single heavy chain variable domain (VH domain or VHH domain) or a single light chain variable domain (VL domain). Hence, the antigen binding site of an immunoglobulin single variable domain is formed by no more than three CDRs. An immunoglobulin single variable domain (ISV) can be a heavy chain ISV, such as a VH (derived from a conventional four-chain antibody), or VHH (derived from a heavy-chain antibody), including a camelized VH or humanized VHH. For example, the immunoglobulin single variable domain may be a (single) domain antibody, a "dAb" or dAb or a Nanobody® ISV (such as a VHH, including a humanized VHH or camelized VH) or a suitable fragment thereof. [Note: Nanobody@ is a registered trademark of Ablynx N. V.]; other single variable domains, or any suitable fragment of any one thereof. "VHH domains", also known as VHHs, VHH antibody fragments, and VHH antibodies, have originally been described as the antigen binding immunoglobulin variable domain of "heavy chain antibodies" (i.e., of "antibodies devoid of light chains"; Hamers-Casterman et al. 1993 (Nature 363:446-448). The term "VHH domain" has been chosen in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHH's, reference is made to the review article by Muyldermans 2001 (Reviews in Molecular Biotechnology 74:277-302).

For the term "dAb's" and "domain antibody", reference is for example made to Ward et al. 1989 (Nature 341:544), to Holt et al. 2003 (Trends Biotechnol. 21:484); as well as to WO 2004/068820, WO 2006/030220, WO 2006/003388. It should also be noted that, although less preferred in the context of the present disclosure because they are not of mammalian origin, single variable domains can be derived from certain species of shark (for example, the so-called "IgNAR domains", see for example WO 2005/18629).

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014 (E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The terms "axial", "radial", or "circumferential" as used herein may be used with respect to a first longitudinal axis of the attachment mechanism, its gripper ring(s), electronic add-on module, the first portion, the second portion, the drug delivery device, the cartridge, the housing, the cartridge holder or the assembly of the drug delivery device and the electronic add-on module, e.g. the axis which extends through the proximal and distal ends of the cartridge.

"Distal" is used herein to specify directions, ends or surfaces which are arranged or are to be arranged to face or point towards dispensing end of the electronic add-on module or the drug delivery device or components thereof and/or point away from, are to be arranged to face away from or face away from the proximal end. On the other hand, "proximal" is used to specify directions, ends or surfaces which are arranged or are to be arranged to face away from or point away from the dispensing end and/or from the distal end of the electronic add-on module or the drug delivery device or components thereof. The distal end may be the end closest to the dispensing and/or furthest away from the proximal end and the proximal end may be the end furthest away from the dispensing end. A proximal surface may face away from the distal end and/or towards the proximal end. A distal surface may face towards the distal end and/or away from the proximal end. The dispensing end may be the needle end where a needle unit is or is to be mounted to the device, for example. Similarly, a distal element compared to a proximal element is located closer to the dispensing end than to the proximal end. Furthermore, when the electronic add-on module is considered alone, the term "distal" may be used with regard to the more distal end of the electronic add-on module, which is located closer to the dispensing end of the drug delivery device when attached to the drug delivery device, and the term "proximal" may be used with regard to the proximal end of the electronic add-on module, which is located further away from the dispensing end of the drug delivery device when attached to the drug delivery device.

BRIEF DESCRIPTION OF THE FIGURES

In the following, non-limiting, examples of the attachment mechanism, the electronic add-on module, the drug delivery device and the assembly of the drug delivery device and the electronic add-on module are described in more detail by making reference to the drawings, in which.

In the Figures, identical elements and components as well as identical elements and components in different examples or embodiments, i.e. elements and components acting identical or provided for the same purposes but belong to different examples, are provided with the same reference signs.

DETAILED DESCRIPTION

Figure 1:
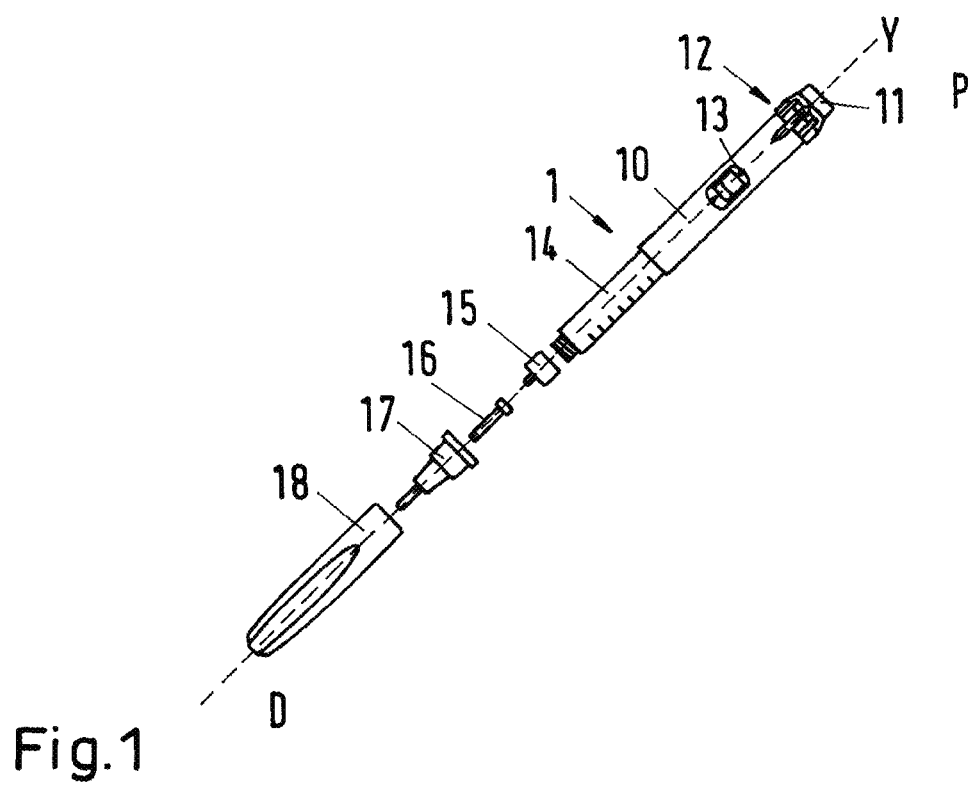
FIG. 1 shows a drug delivery device.

FIG. 1 shows an exploded view of an exemplary medicament or drug delivery device 1. The drug delivery device 1 is a pen-type injector comprising a housing 10 in which a drive mechanism for dose setting and dose dispensing is arranged. The drug delivery device 1 extends from a distal point to a proximal direction P or from a proximal point to a distal direction D along a longitudinal axis Y of the drug delivery device 1. In order to set a dose for delivery a user may rotate or dial a dose dial grip 12 with respect to the housing 10, wherein the dose dial grip 12 is arranged at or near a proximal end of the housing 10. During dose setting the dose dial grip 12 may perform a helical movement, i.e. a combined axial and rotational movement, or may perform pure rotational movement.

The drive mechanism of the drug delivery device 1 may comprise a plunger, a drive sleeve, a clutch, a clutch spring, a number sleeve, a last dose nut and so on, which may move during dose setting and/or dose dispensing. Although not all of these components are shown in detail, for example, the drive mechanisms disclosed in EP 1 570 876, EP 2 814 547, U.S. Pat. No. 9,937,294 B2 or WO 2004/078239 A1 represent suitable drive mechanisms for the present disclosure.

Once the dose is set by means of the dose dial grip 12, the user may press a dose button 11 arranged at the proximal end of the drug delivery device 1 in the distal direction D in order to dispense the dose. When pressing the dose button 11, the user applies a force directed towards the proximal end of the drug delivery device 1, wherein the force moves the dose button 11 in the distal direction of the pen and parallel to the longitudinal axis Y. This axial movement of the dose button 11 releases the drive mechanism for example by de-coupling a number sleeve from the drive sleeve, wherein irrespective of which component of the drug delivery device 1 performs a rotational movement during dose delivery, the dose dial grip 12 is coupled to a respective component in order to perform a rotational movement during dose delivery.

This rotational movement of the dose dial grip 12 during dose delivery may be used to determine, for example, the actual dose delivered by means of an electronic add-on module 100 as shown in in FIGS. 2 and 3 and described here below.

The exemplary drug delivery device 1 shown in FIG. 1 comprises in addition to the dose dial grip 12 and the dose button 11 an optional dosage window 13, a container 14, and a needle 15. The set dose may be displayed via the dosage window 13. The container 14 may be filled directly with a drug, for example insulin, or may be configured to receive a cartridge and thus act as a cartridge holder. The needle 15 may be affixed to the container or the receptacle. During dose dispensing the drug is dispensed through the needle 15. The needle 15 may be protected by an inner needle cap 16. In addition, the needle 15 may be protected by an outer cap 17 and/or drug delivery device cap 18.

In order for an electronic add-on module 100 to be functionally attached to a drug delivery device 1, i.e. attached and usable, either the drug delivery device 1 can be adapted to the electronic add-on module 100 or, conversely, the electronic add-on module 100 can be adapted to the drug delivery device 1. Regardless of this, the drug delivery device 1 as well as the electronic add-on module 100 may have different examples, wherein the further description with respect to the drug delivery device 1 essentially deals with the dose button 11, the dose dial grip 12 and the drive sleeve inside the housing 10.

Figure 2:
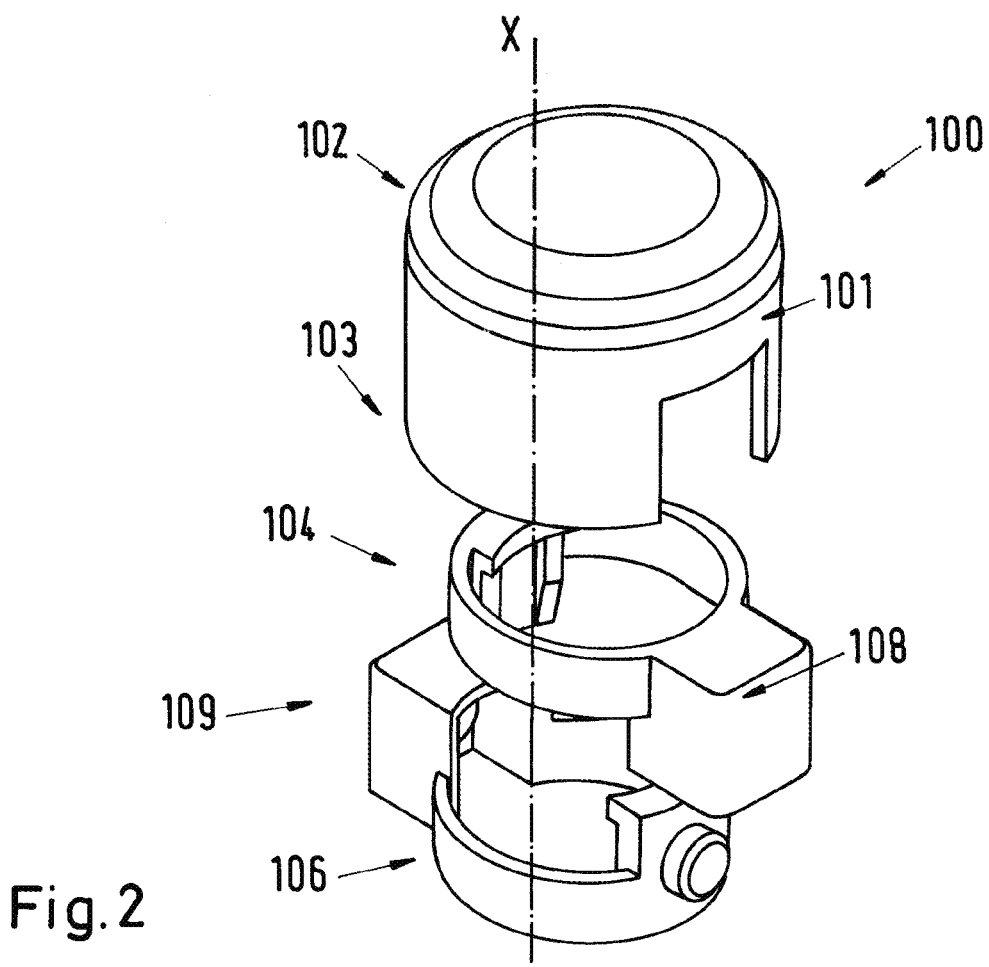
FIG. 2 shows an exploded view of an attachment mechanism according to the present disclosure.
Figure 3:
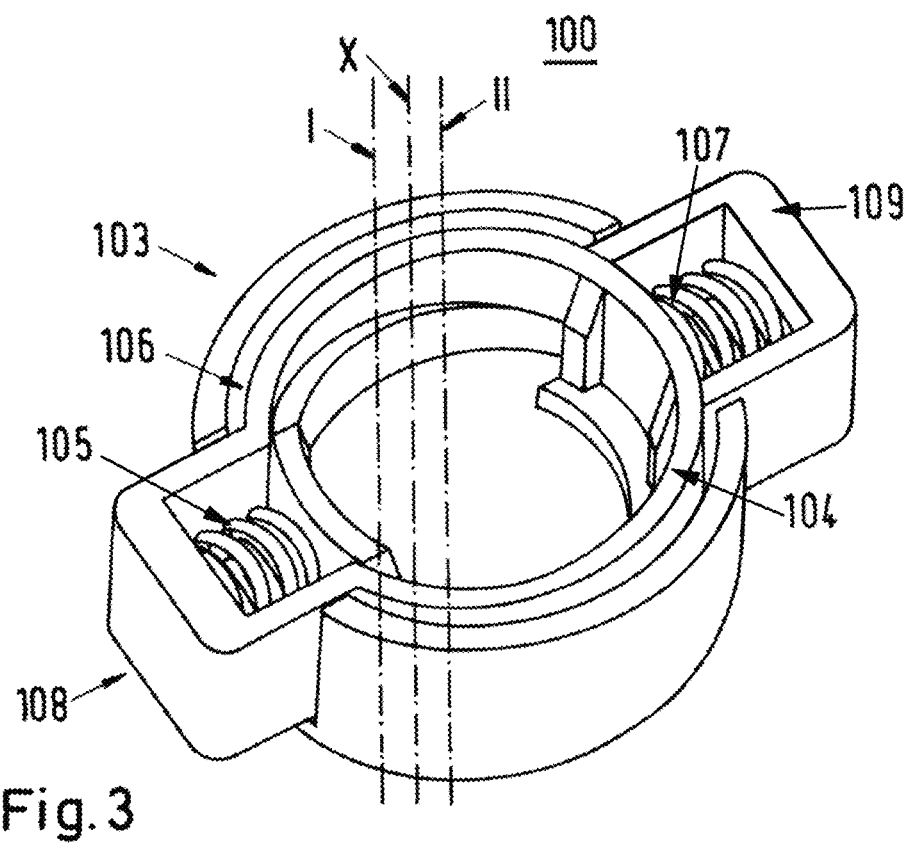
FIG. 3 shows a bottom view of the mechanism of FIGS. 2.
Figure 4:
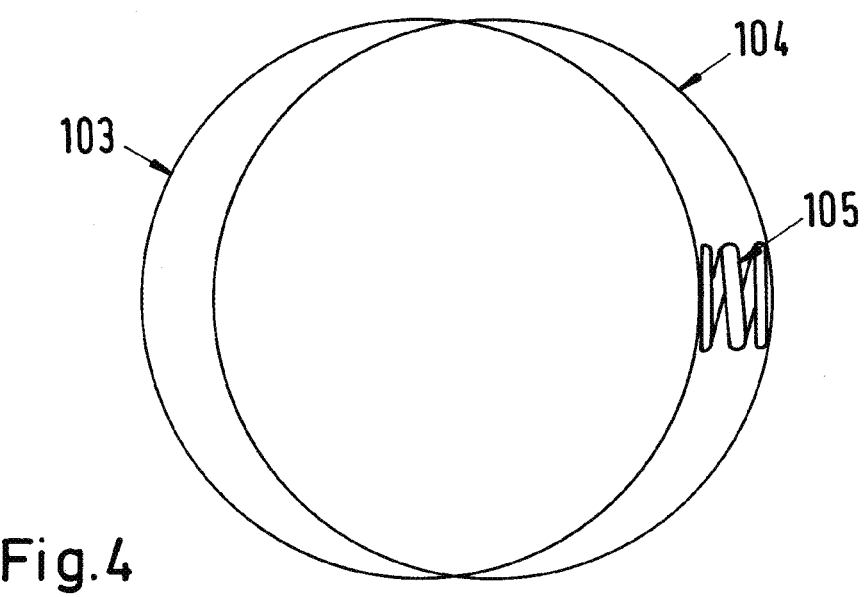
FIG. 4 schematically shows a further embodiment of an attachment mechanism according to the present disclosure.

FIGS. 2 to 4 show exemplary embodiments of an electronic add-on module 100 suitable for releasable attachment to a user interface of drug delivery device 1. The module 100 substantially comprises a first portion 101 and a second portion 102 which are coaxially arranged on a longitudinal axis X coinciding with the longitudinal axis Y of the drug delivery device when attached to each other.

The first portion 101 comprises a main housing 103 receiving the second portion 102. Although not depicted in detail, the second portion 102 may comprise in a button housing a printed circuit board assembly (PCBA), a sensor arrangement, e.g. comprising a microphone, a communication unit and a battery. The main housing 103 is a sleeve-like component with an inwardly protruding, ring-shaped flange at its proximal end which limits axial movement of the second portion 102 in the proximal direction. A spring (not shown), e.g. a compression spring, is arranged between an inner flange of the first portion and an end face of the second portion, thereby biasing the second portion upwards, i.e. proximally, as seen in FIGS. 2.

The first portion 101 of the module 100 comprises an attachment mechanism suitable for fastening the module on the drug delivery device 1, especially on the dose dial grip 12. The attachment mechanism of the first embodiment depicted in FIGS. 2 and 3 comprises the housing 103, a first gripping ring 104 with a longitudinal axis I and with a first spring 105 and a second gripping ring 106 with a longitudinal axis II and with a second spring 107. The gripping rings 104, 106 have smaller diameter than the housing 103 and are substantially encased in the housing 103. A button portion 108 of the first gripping ring 104 constitutes an actuator for shifting the ring 104 radially inwards. The button portion 108 protrudes radially through a cut-out in the housing 103. A button portion 109 of the second gripping ring 106 forms an actuator and is located diametrically opposite to the button portion 108 of the first gripping ring 104 and protrudes radially through a further cut-out in the housing 103.

As depicted in FIGS. 2 and 3, the gripping rings 104, 106 are arranged one behind the other along the longitudinal axis X of the module 100. The button portions 108, 109 may have a length in the direction of the longitudinal axis X which is substantially the combined length of both gripping rings 104, 106. However, other configurations and dimensions of the button portions are suitable for achieving the same functionality.

The gripping rings 104, 106 are retained within the housing 103 such that they can slide along one radial axis which may be perpendicular to the longitudinal axis X of the module 100 but are constrained otherwise. In the neutral state of the attachment mechanism, i.e. in the clamping condition, as depicted in FIG. 3, the springs 105, 107 expand and push the rings 104, 106, more specifically the sides opposite of the respective button portions 108, 109, closer together. This reduces the inner diameter defined by the two gripping rings. In other words, the longitudinal axes I, II of each gripping ring 104, 106 are slightly offset from each other and from the longitudinal axis X of the module 100 when the attachment mechanism is in the clamping condition.

On the other hand, by pressing the two side button portions 108, 109 the user can compress the springs 105, 107 and increase the distance between the rings 104, 106, widening the gripper portion's opening and enabling attachment to an injector pen dial grip 12 of arbitrary size. The attachment mechanism is in its open condition when the button portions are fully pressed in. For example, the longitudinal axes I, II of each gripping ring 104, 106 may coincide with each other and with the longitudinal axis X of the module 100 when the attachment mechanism is in the open condition.

In other words, to connect the attachment mechanism or a module with such an attachment mechanism to a dial grip 12 or the like component part of a drug delivery device 1, the user presses the button portions 108, 109 on either side of the mechanism to widen the opening, before then placing the mechanism or module onto the dial grip 12 and letting go of the button portions. The force of the springs 105, 107 shifts the gripping rings 104, 106 back into the clamping condition of the attachment mechanism.

This spring force combined with the geometry of the gripper rings enables a secure connection across a range of pen diameters. The springs 105, 107 may be configured to have a holding torque of at least 750 Nmm, e.g. between 1.250 Nmm and 2.500 Nmm or between 1.000 Nmm and 1.500 Nmm, for example about or exactly 1.350 Nmm, when attached to a dial grip 12 or the like component part having a diameter of about 14 mm to 18 mm and when being in its clamping condition.

FIG. 4 depicts the attachment mechanism of an alternative embodiment comprising only one gripping ring 104 guided in the housing 103 to permit radial shifting movement between the open condition and the clamping condition and vice versa. In this embodiment, only one spring 105, e.g. a compression spring, is required which may be interposed between a radially outer surface of the housing 103 and a radially inner surface of the first gripping ring 104. In a similar manner as described with reference to the first embodiment, the spring 105 biases the gripping ring 104 into the clamping condition in which a portion of the inner wall of the housing 103 and the side of the ring opposite to the button portion 105 reduces an inner diameter of the mechanism. Again, the mechanism may be shifted into the open condition by pressing the button portion 108 radially inwards against the force of the spring 105, thereby widening the inner diameter.

REFERENCE NUMERALS

1 drug delivery device
10 housing
11 dose button
12 dose dial grip
13 display window
14 container
15 needle
16 inner needle cap
17 outer cap
18 drug delivery device cap
100 electronic add-on module
10° first portion
102 second portion
103 housing
104 (first) gripping ring
105 (first) spring
106 (second) gripping ring
107 (second) spring
108 button portion of ring 104
109 button portion of ring 106
D distal direction
P proximal direction
I longitudinal axis of the first ring 104
II longitudinal axis of the second ring 106
X (first) longitudinal axis of the module 100
Y longitudinal axis of the drug delivery device 1

The invention claimed is:

1. An electronic add-on module configured to be releasably attached to a drug delivery device, the electronic add-on module comprising:
    a housing defining a first longitudinal axis;
    a gripping portion comprising:
        a first gripping ring defining a first ring longitudinal axis parallel to the first longitudinal axis of the housing, the first gripping ring being retained in the housing such that the first gripping ring is shiftable in a first direction perpendicular to the first longitudinal axis of the housing from an open condition in which the first longitudinal axis of the housing is a first distance from the first ring longitudinal axis to a clamping condition in which the first longitudinal axis of the housing is a second distance from the first ring longitudinal axis, the second distance being greater than the first distance; and
        at least one spring configured to bias the first gripping ring into the clamping condition; and
    an actuator for operating the first gripping ring between the open condition and the clamping condition.

2. The electronic add-on module according to claim 1, wherein the housing comprises a first portion and the electronic add-on module comprises a second portion coupled to the first portion and configured to allow relative axial movement of the second portion parallel to the first longitudinal axis of the housing with respect to the first portion.

3. The electronic add-on module according to claim 2, wherein:
    the first portion defines an auxiliary dose dial user interface configured to be attached to a dose dial user interface of the drug delivery device such that the first portion is configured to follow a movement of the dose dial user interface and the dose dial user interface is configured to follow a movement of the first portion when the electronic add-on module is attached to the drug delivery device, and
    the second portion defines an auxiliary injection user interface configured to apply pressure onto an injection user interface of the drug delivery device.

4. The electronic add-on module according to claim 2, wherein the second portion comprises:
an electrical power source,
a printed circuit board assembly,
a sensor arrangement configured to detect a relative rotational movement between at least two component parts of the drug delivery device,
a communication unit for communicating with another device, and/or
a switch arrangement.

5. The electronic add-on module according to claim 4, wherein the second portion comprises the sensor arrangement, and the sensor arrangement comprises an acoustic sensor arrangement.

6. The electronic add-on module according to claim 2, further comprising a spring configured to bias the second portion in a proximal direction with respect to the first portion.

7. An assembly comprising:
a drug delivery device comprising:
  a device housing configured to receive a container for a drug;
  a dose setting unit comprising a dose dial user interface at least rotationally movable with respect to the device housing during dose setting and an injection user interface at least axially moveable with respect to the device housing for causing dose dispensing; and
  a dose delivery unit comprising a plunger at least axially movable with respect to the device housing during the dose dispensing; and
an electronic add-on module configured for attachment to the drug delivery device, the electronic add-on module comprising:
  a module housing defining a first longitudinal axis;
  a gripping portion comprising:
    a first gripping ring defining a first ring longitudinal axis parallel to the first longitudinal axis of the module housing, the first gripping ring being shiftable from an open condition to a clamping condition; and
    at least one spring configured to bias the first gripping ring into the clamping condition; and
  an actuator for operating the first gripping ring between the open condition and the clamping condition,
wherein the first gripping ring of the electronic add-on module is configured to abut the dose dial user interface in a form fit and/or a friction fit when the electronic add-on module is attached to the dose dial user interface of the drug delivery device and when the first gripping ring is in the clamping condition, and
wherein the first gripping ring is retained in the module housing such that the first gripping ring is shiftable in a first direction perpendicular to the first longitudinal axis of the module housing from the open condition in which the first longitudinal axis of the module housing is a first distance from the first ring longitudinal axis to the clamping condition in which the first longitudinal axis of the module housing is a second distance from the first ring longitudinal axis, wherein the second distance is greater than the first distance.

8. The assembly according to claim 7, wherein the container is a cartridge.

9. The assembly according to claim 7, wherein the drug delivery device further comprises a clicker mechanism configured to generate an acoustic feedback signal at least during the dose setting.

* * * * *